(12) United States Patent
Tanaka

(10) Patent No.: US 8,480,568 B2
(45) Date of Patent: Jul. 9, 2013

(54) ENDOSCOPE APPARATUS WITH AUTOMATIC SELECTION BETWEEN AUTOMATED INSERTION DIRECTION SEARCH METHODS

(75) Inventor: Hideki Tanaka, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 173 days.

(21) Appl. No.: 13/026,753

(22) Filed: Feb. 14, 2011

(65) Prior Publication Data

US 2011/0237889 A1 Sep. 29, 2011

Related U.S. Application Data

(63) Continuation of application No. PCT/JP2010/062513, filed on Jul. 26, 2010.

(30) Foreign Application Priority Data

Sep. 30, 2009 (JP) ................................. 2009-228024

(51) Int. Cl.
*A61B 1/00* (2006.01)
(52) U.S. Cl.
USPC ............................ 600/146; 600/117; 600/118
(58) Field of Classification Search
USPC ................. 600/117, 118, 139, 141, 145, 146, 600/152; 606/130
See application file for complete search history.

(56) References Cited

U.S. PATENT DOCUMENTS

| | | | | |
|---|---|---|---|---|
| 5,347,987 | A | * | 9/1994 | Feldstein et al. ............... 600/109 |
| 7,089,928 | B2 | * | 8/2006 | Besharim et al. ......... 128/200.26 |
| 2002/0062062 | A1 | * | 5/2002 | Belson et al. ................. 600/146 |
| 2005/0010082 | A1 | * | 1/2005 | Nishimura et al. ........... 600/145 |
| 2009/0149711 | A1 | * | 6/2009 | Tanaka et al. ................. 600/152 |

FOREIGN PATENT DOCUMENTS

| | | |
|---|---|---|
| EP | 1 437 083 A1 | 7/2004 |
| EP | 2 070 465 A1 | 6/2009 |
| EP | 2 215 960 A1 | 8/2010 |
| JP | 2003-093328 | 4/2003 |
| JP | 2009-131406 | 6/2009 |
| JP | 2010-088573 | 4/2010 |
| WO | WO 2008/155828 A1 | 12/2008 |
| WO | WO 2009/069395 A1 | 6/2009 |

OTHER PUBLICATIONS

European Search Report dated Feb. 13, 2012 from corresponding European Patent Application No. EP 10 82 0231.8.

* cited by examiner

*Primary Examiner* — Katherine Dowe
*Assistant Examiner* — Aaron B Fairchild
(74) *Attorney, Agent, or Firm* — Scully, Scott, Murphy & Presser, P.C.

(57) ABSTRACT

An endoscope apparatus includes an endoscope which has an insertion portion which is provided with a distal end portion and a bendable bending portion at a distal end side and is inserted into a body cavity of a subject, a relative position calculation section which calculates a relative position of the distal end portion in the body cavity to the subject, a selection section which selects a search method corresponding to the position detected from a plurality of search methods for searching for a bending direction of the bending portion, based on the calculated relative position, a bending direction determination section which determines the bending direction of the bending portion according to the selected search method, and a bending drive section which bends and drives the bending portion based on the determined bending direction.

14 Claims, 12 Drawing Sheets

| | FIXED | SUBSTANTIALLY LINEAR | ALONG FRONTAL PLANE | POSITION (INSERTION LENGTH) | SEARCH METHOD |
|---|---|---|---|---|---|
| RECTUM | ○ | × | ○ | La | FIRST |
| SIGMOID COLON | × | × | △ | Lb | SECOND |
| DESCENDING COLON | ○ | ○ | ○ | Lc | FIRST |
| SPLENIC FLEXURE | ○ | × | ○ | Ld | FIRST |
| TRANSVERSE COLON | × | × | △ | Le | SECOND |
| HEPATIC FLEXURE | ○ | × | ○ | Lf | FIRST |
| ASCENDING COLON | ○ | ○ | ○ | Lg | FIRST |

ENDOSCOPE APPARATUS WITH AUTOMATIC SELECTION BETWEEN AUTOMATED INSERTION DIRECTION SEARCH METHODS

CROSS REFERENCE TO RELATED APPLICATION

This application is a continuation application of PCT/JP2010/062513 filed on Jul. 26, 2010 and claims benefit of Japanese Application No. 2009-228024 filed in Japan on Sep. 30, 2009, the entire contents of which are incorporated herein by this reference.

BACKGROUND OF THE INVENTION

1. Field of the Invention

The present invention relates to an endoscope apparatus for performing endoscopy by inserting an insertion portion which is provided with a bending portion at a distal end side, into a body cavity.

2. Description of the Related Art

In recent years, endoscopes which enable endoscopy and the like with insertion portions, which are provided with observation means at the distal end portions, inserted into subjects have been widely used in the medical field and the like.

Meanwhile, when an insertion portion is inserted into a body cavity in a complicatedly curved shape like a large intestine, for example, a skilled insertion manipulation is sometimes required.

Endoscope insertion manipulation is basically performed so that the distal end of the insertion portion is inserted toward the direction in which a body cavity (tube cavity) extends, but if a sharply curved site is present, for example, a tube cavity dark part (also simply called a dark part) to be a target position in the direction in which a tube cavity extends sometimes disappears from an observation field of view of the endoscope.

Therefore, in order to support the insertion manipulation, for example, the first conventional example of Japanese Patent Application Laid-Open Publication No. 200393328 discloses the apparatus and the method for detecting (searching for) the direction of extension of the tube cavity in which the endoscope should be inserted even when a dark part disappears, by using gradient information of brightness and darkness in an endoscopic image.

Further, the second conventional example of International Publication No. 2008/155828 stores the positional information of a dark part, and detects an insertion direction based on the positional information of the dark part which is captured in the past, if the dark part disappears.

SUMMARY OF THE INVENTION

An endoscope apparatus of one aspect of the present invention includes an endoscope which has an insertion portion provided with a distal end portion and a bendable bending portion at a distal end side, and is inserted into a body cavity of a subject, a relative position calculation section which calculates a relative position of the distal end portion in the body cavity to the subject, a selection section which selects a search method corresponding to the relative position from a plurality of search methods for searching for a bending direction of the bending portion, based on the calculated relative position, a bending direction determination section which determines the bending direction of the bending portion according to the search method selected by the selection section, and a bending drive section which bends and drives the bending portion based on the bending direction determined by the bending direction determination section.

DETAILED DESCRIPTION OF THE PREFERRED EMBODIMENT(S)

Hereinafter, embodiments of the present invention will be described with reference to the drawings.

First Embodiment

Figure 1:
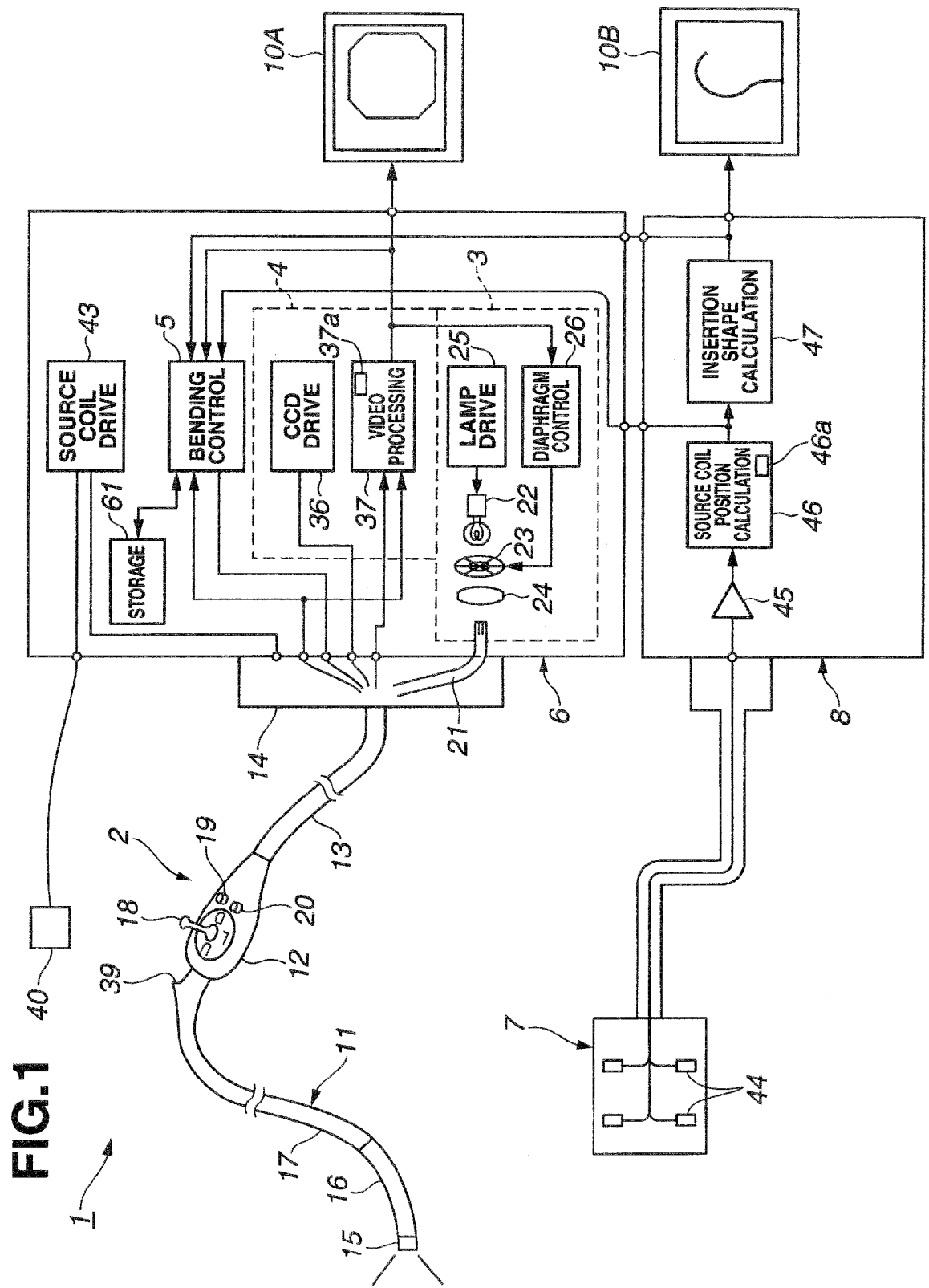
FIG. 1 is a diagram showing a configuration of a front end of an endoscope apparatus according to a first embodiment of the present invention.

As shown in FIG. 1, an endoscope apparatus 1 according to a first embodiment of the present invention has an endoscope 2 which is inserted into a body cavity or the like, and a video processor 6 which contains a light source section 3 which supplies an illuminating light to the endoscope 2, a signal processing section 4 which performs signal processing for image pickup means contained in the endoscope 2, a bending control section 5 which performs bending control of a bending portion of the endoscope 2, and the like.

The endoscope apparatus 1 further has a sense coil unit 7 which performs detection of a position of a source coil for positional detection provided in the endoscope 2, an insertion form detection apparatus 8 which generates an image of an insertion form of the endoscope 2 according to a detection signal from the sense coil unit 7, and monitors 10A and 10B which respectively display an endoscopic image picked up by the image pickup means and an insertion form detection image by the insertion form detection apparatus 8.

The endoscope 2 has an elongated insertion portion 11 which is inserted into a body cavity, an operation portion 12 which is provided at a rear end of the insertion portion 11, and a universal cord 13 which is extended from the operation portion 12, and a connector 14 at a rear end of the universal cord 13 is attachably and detachably connected to the video processor 6.

Further, the insertion portion 11 has a rigid distal end portion 15 provided at a distal end thereof, a bending portion 16 which is bendably provided adjacently to a rear end of the distal end portion 15, and a flexible tube portion 17 which has flexibility and a long length extending to a front end of the operation portion 12 from a rear end of the bending portion 16.

The operation portion 12 is provided with a bending joystick 18 which performs an instruction operation of a bending direction and a bending angle for the aforesaid bending portion 16, a search instruction switch 19 which performs instruction operations of search start for searching an insertion direction and search stop, when a dark part disappears and the insertion direction is not found while the insertion portion 11 is inserted into a body cavity, and an insertion mode selection switch 20 which performs selection of an automatic insertion mode and a manual insertion mode.

A light guide 21 which transmits an illuminating light is inserted through the inside of the insertion portion 11 and the like of the endoscope 2, and a rear end of the light guide 21 is projected from the connector 14 and is an incident end face.

An illuminating light by a lamp 22 contained in the light source section 3 is incident on the incident end face through a diaphragm 23 and a condensing lens 24. The lamp 22 is lit by a lamp drive power supplied from a lamp drive circuit 25, and generates the illuminating light.

Further, the diaphragm 23 has an opening amount (diaphragm amount) for passing the illuminating light controlled by a diaphragm control circuit 26.

The illuminating light which is transmitted by the light guide 21 further passes through an illumination lens 27 (see FIG. 2) attached to an illuminating window from a light guide front end face fixed to the distal end portion 15 of the insertion portion 11 and exits outside to illuminate an object such as a diseased part in a body cavity.

Figure 2:
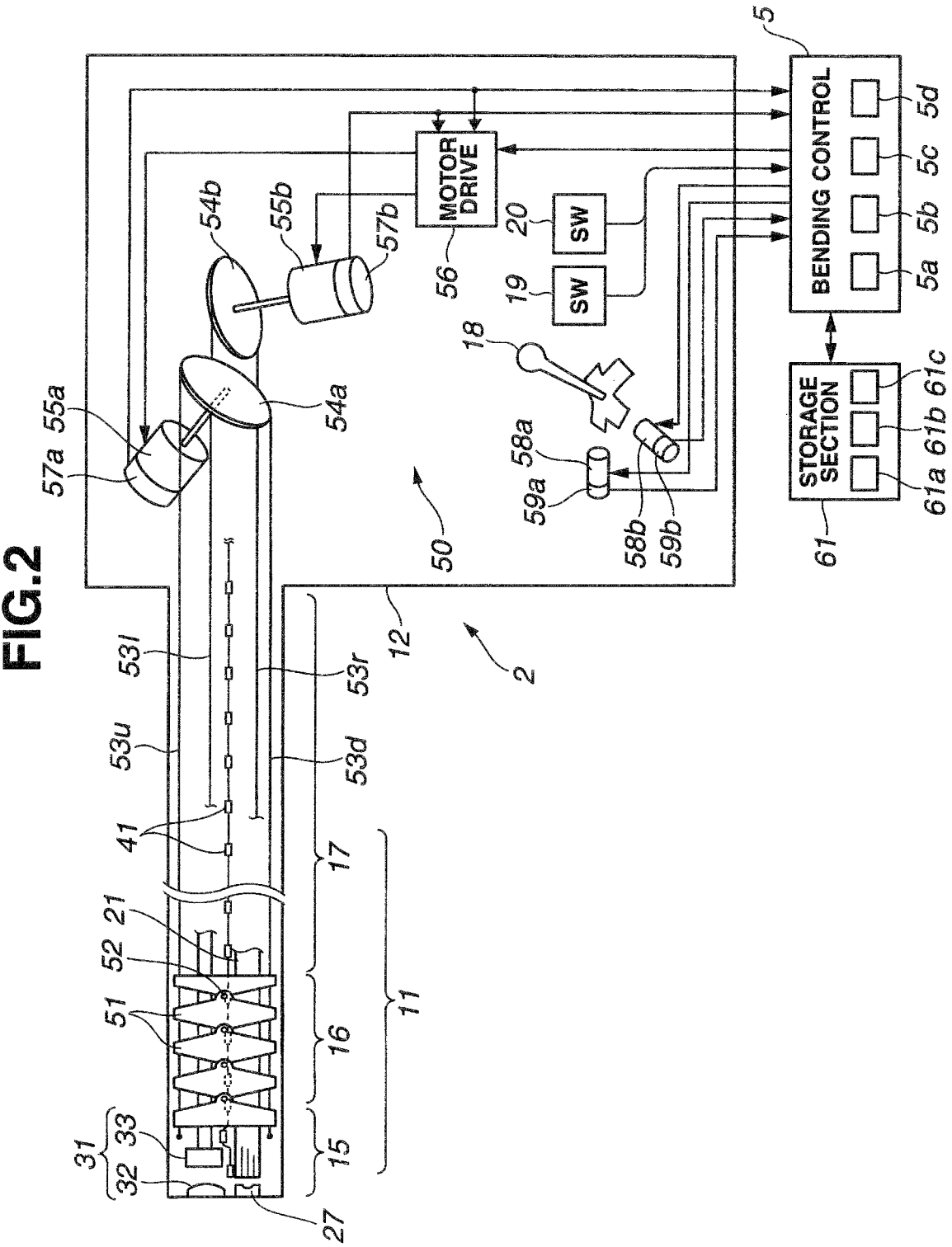
FIG. 2 is a diagram showing a configuration of an endoscope and a bending drive mechanism.

As shown in FIG. 2, the distal end portion 15 is provided with an observation window (adjacently to the illuminating window), and an image pickup unit 31 is attached to the observation window.

The image pickup unit 31 has an objective lens 32 which is attached to a lens frame not illustrated and forms an optical image of an object, and a charge coupled device (abbreviated as CCD) 33 as an image pickup device with an image pickup surface thereof disposed at an image forming position by the objective lens 32.

A cable connected to the CCD 33 is inserted through the inside of the insertion portion 11 and the like, and its rear end side is connected to a CCD drive circuit 36 and a video processing circuit 37 which configure the signal processing section 4 through an electric contact point of the connector 14 as shown in FIG. 1.

The CCD drive circuit 36 generates a CCD drive signal, and applies the CCD drive signal to the CCD 33. The CCD 33 photoelectrically coverts the optical image formed on the image pickup surface by application of the CCD drive signal, and outputs the converted image as a CCD output signal.

The CCD output signal is inputted in the video processing circuit 37, and the video processing circuit 37 generates a video signal for displaying an optical image of the image pickup surface of the CCD 33 as an endoscopic image, and outputs the video signal to the monitor 10A, whereby the endoscopic image is displayed on a display screen of the monitor 10A.

The CCD 33 is disposed to have a predetermined relationship with the bending direction of the bending portion 16 in the distal end portion 15. More specifically, an upper direction of the image pickup surface of the CCD 33 is matched with an upper direction of the bend of the bending portion 16.

Further, the video signal is inputted in the diaphragm control circuit 26, and the diaphragm control circuit 26 calculates an average brightness by integrating a luminance signal component of the video signal at predetermined periods. The diaphragm control circuit 26 modulates the opening amount of the diaphragm 23 with a signal of the difference which is obtained by subtracting a reference value corresponding to a suitable brightness from the signal of the average brightness set as a diaphragm control signal. The diaphragm control circuit 26 performs automatic light modulation so that the illuminating light amount which passes through the diaphragm 23 becomes the reference value.

Further, the video processing circuit 37 has a dark part detection circuit 37a which detects presence or absence of a dark part in an endoscopic image by image processing. Detection (determination) information of the presence or absence of the dark part by the dark part detection circuit 37a is sent to the bending control section 5.

When the mode is set at an automatic insertion mode for automatically inserting the insertion portion 11, if the dark part disappears, the bending control section 5 shifts the mode to a search mode for searching the dark part as a target position as an insertion direction (in which the distal end portion 15 should be inserted, or the distal end portion 15 should be directed), and when a dark part is detected in the search mode, the bending control section 5 stops the search mode and returns the mode to the automatic insertion mode for automatically inserting the insertion portion 11 with the dark part as the target position.

Further, in a manual insertion manipulation, if a surgeon operates the search instruction switch 19 in the case of disappearance of a dark part, the bending control section 5 shifts the mode to the search mode for searching a dark part. When a dark part is detected in the search mode, the bending control section 5 stops the search mode, and returns to the manual insertion manipulation.

A treatment instrument channel not illustrated is provided in the insertion portion 11, and a rear end side of the treatment instrument channel communicates with a treatment instrument insertion port 39 provided in the vicinity of a front end of the operation portion 12.

Further, the bending portion 16 is provided adjacently to a rear end of the distal end portion 15 of the insertion portion 11, and the bending control section 5 provided inside the video processor 6 is configured to perform control of an electrically-driven bending drive mechanism 50 as shown in FIG. 2.

A plurality of bending pieces 51 which configure the bending portion 16 have portions adjacent to one another in a longitudinal direction of the bending portion 16 connected rotatably by rivets 52.

Each of the bending pieces 51 has the bending direction fixed according to the position where the rivet 52 is provided, and in this case the rivets 52 are disposed at lateral positions and vertical positions alternately or at proper intervals, so as to be bendable in the vertical direction and the lateral direction.

FIG. 2 shows only the rivets 52 which are bent in the vertical direction by simplification. Further, angel wires (bending wires) 53u and 53d, and 53l and 53r which are bent in the vertical direction and the lateral direction are inserted through the insertion portion 11, and distal ends of the angle wires 53u and 53d, and 53l and 53r are fixed to the distal end portion 15.

Further, rear ends of the angle wires 53u and 53d, 53l and 53r are fixed to a vertically bending pulley 54a and a laterally bending pulley 54b which are disposed in the operation portion 12.

The pulleys 54a and 54b are reversibly rotated by electric motors 55a and 55b which configure bending drive means which electrically bends and drives. The electric motors 55a and 55b are driven by a motor drive signal by a motor drive section 56. The motor drive section 56 is controlled by the bending control section 5.

FIG. 1 shows a configuration example in which the bending control section 5 is provided inside the video processor 6, but the bending control section 5 may be provided inside the endoscope 2, such as an inside of the operation portion 12.

The electric motors 55a and 55b which are driven by the motor drive signal by the motor drive section 56 rotate the pulleys 54a and 54b, pull the angle wires 53u, 53d, 53l and 53r by the rotation of the pulleys 54a and 54b to bend and drive the bending portion 16.

When the pulleys 54a and 54b are rotated, the amounts of pulling of the angle wires 53u, 53d, 53l and 53r are determined in correspondence with the rotational angles of the pulleys 54a and 54b, and the bending portion 16 is bent in correspondence with the amounts of pulling. Accordingly, the rotational angles of the electric motors 55a and 55b or the pulleys 54a and 54b, or the amounts of pulling (amounts of moving) of the angle wires 53u, 53d, 53l and 53r are detected, whereby the bending angle of the bending portion 16 can be detected.

The present embodiment adopts the configuration which detects the bending angle of the bending portion 16 via the rotational angles of the pulleys 54a and 54b by rotary encoders (hereinafter, abbreviated as encoders) 57a and 57b which are attached to shaft portions of the electric motors 55a and 55b, for example.

More specifically, based on output signals of the encoders 57a and 57b, the rotational angles of the pulleys 54a and 54b, in other words, the bending angle of the bending portion 16 corresponding to the rotational angles of the pulleys 54a and 54b can be detected. Accordingly, the encoders 57a and 57b form bent shape detection means which detects a bent shape of the bending portion 16.

Detection signals (detection values) of the pulley angles or the bending angles based on the output signals from the encoders 57a and 57b are inputted in the motor drive section 56. The motor drive section 56 receives instruction values of a bending instruction direction and the bending angle by a joystick 18 as bending instruction operation means via the bending control section 5.

The motor drive section 56 rotationally drives the electric motors 55a and 55b so that the detection values by the encoders 57a and 57b follow (correspond to) the instruction values.

The bending control section 5 gives the instruction value by the vending instruction operation means to the motor drive section 56, and the motor drive section 56 rotationally drives the electric motors 55a and 55b to bend the bending portion 16 to an instructed predetermined bending angle so that the detection value of the bending angle becomes the instruction value.

The surgeon performs a tilting operation in an optional bending direction of vertical and lateral directions by the joystick 18 as the bending instruction operation means provided at the operation portion 12, whereby the tilting direction becomes a bending instruction direction and the tilting angle becomes the instruction value of the bending angle.

The surgeon performs an instruction operation of tilting the joystick 18 in an optional direction of the vertical and the lateral directions, whereby a vertical direction joystick motor 58a and a lateral direction joystick motor 58b rotate in correspondence to the tilting direction.

The encoders 59a and 59b detect the rotational angles, and detection signals from the encoders 59a and 59b are inputted in the bending control section 5 as the information of the bending directions and the instruction values of the bending angle. The joystick motors 58a and 58b are controlled by the bending control section 5, and the detection signals from the encoders 59a and 59b are also inputted in the bending control section 5. The bending control section 5 outputs the information of the bending directions and the instruction values of the bending angle as the detection signals from the encoders 59a and 59b to the motor drive section 56, and controls the operation thereof.

Further, in the insertion portion 11, the source coils 41 are disposed, for example, at predetermined intervals, along a longitudinal direction of the insertion portion 11, and a signal line connected to the source coils 41 is connected to a source coil drive circuit 43 provided in the video processor 6, through the electric contact point of the connector 14 as shown in FIG. 1.

The source coil drive circuit 43 sequentially applies an AC drive signal to each of the source coils 41 through the signal line, and generates an AC magnetic field around each of the source coils 41.

Further, a sense coil unit 7 constituted of a plurality of sense coils 44 is disposed at a predetermined position in a peripheral portion of a bed where a patient not illustrated into which the insertion portion 11 is inserted is lying as shown in FIG. 1, and a plurality of sense coils 44 detect magnetic fields generated by the source coils 41 disposed in the insertion portion 11.

The detection signal by the sense coil 44 is amplified by an amplifier 45 in the insertion form detection apparatus 8, and thereafter, is inputted in a source coil position calculation circuit 46, and the source coil position calculation circuit 46 calculates a position of each of the source coils 41 from the amplified value and the phase value in the signal detected by the sense coil 44.

The positional information calculated by the source coil position calculation circuit 46 is inputted in an insertion form calculation circuit 47. The insertion form calculation circuit 47 detects the insertion form of the insertion portion 11 which is inserted into a body cavity from a shape obtained by connecting the positions of the respective source coils 41 which are calculated, models the detected insertion form and generates an insertion form image signal.

The generated insertion form image signal is inputted in the monitor 10B, and the insertion form image is displayed on a display screen of the monitor 10B.

As shown in FIG. 2, the source coils 41 are also attached in the distal end portion 15, and the source coil position calculation circuit 46 calculates a specific direction in the vertical and lateral directions and the like in the circumferential direction of the distal end portion 15 in addition to the position of the distal end portion 15, from the positions of a plurality of source coils 41 attached to the distal end portion 15. In the distal end portion 15, a plurality of source coils 41 are disposed in the arrangement relation out of the straight line so as to be able to detect the circumferential direction of the distal end portion 15.

By the arrangement of a plurality of source coils 41 in the distal end portion 15, the upper direction of the CCD 33 (this corresponds to the upper direction of bending) becomes detectable, in addition to the position and the longitudinal direction (also called the distal end portion direction) of the distal end portion 15. The source coil position calculation circuit 46 outputs the information of the positions and the directions of a plurality of source coils 41 in the distal end portion 15 to the bending control section 5.

The bending control section 5 has a function of detecting the distal end portion direction and a reference direction (more specifically, the upper direction) in the case of performing observation or bending as well as the position of the distal end portion 15 in a body cavity from the inputted information of the positions and the directions of a plurality of source coils 41 in the distal end portion 15.

More specifically, the bending control section 5 has a function of a position detection section 5a which detects the position of the distal end portion 15 in the body cavity into which the insertion portion 11 is inserted. The source coil position calculation circuit 46 may be configured to have the function of the position detection section which detects the position and the like of the distal end portion 15, and the bending control section 5 may be configured to use the information thereof.

Further, as shown in FIG. 1, the endoscope apparatus 1 includes a patient plate 40, and the patient plate 40 is connected to the source coil drive circuit 43. The patient plate 40 is used for detection of a body position of a patient 62 by being placed at an abdomen or the like of the patient 62 (see FIG. 4). For example, three source coils not illustrated are provided on a plate plane inside the patient plate 40, and are driven by the source coil drive circuit 43.

The source coil position calculation circuit 46 detects the positions of the three source coils of the patient plate 40, and thereby, detects the plane of the patient plate 40 to detect the body position of the patient 62 from the plane.

Figures 3, 4:
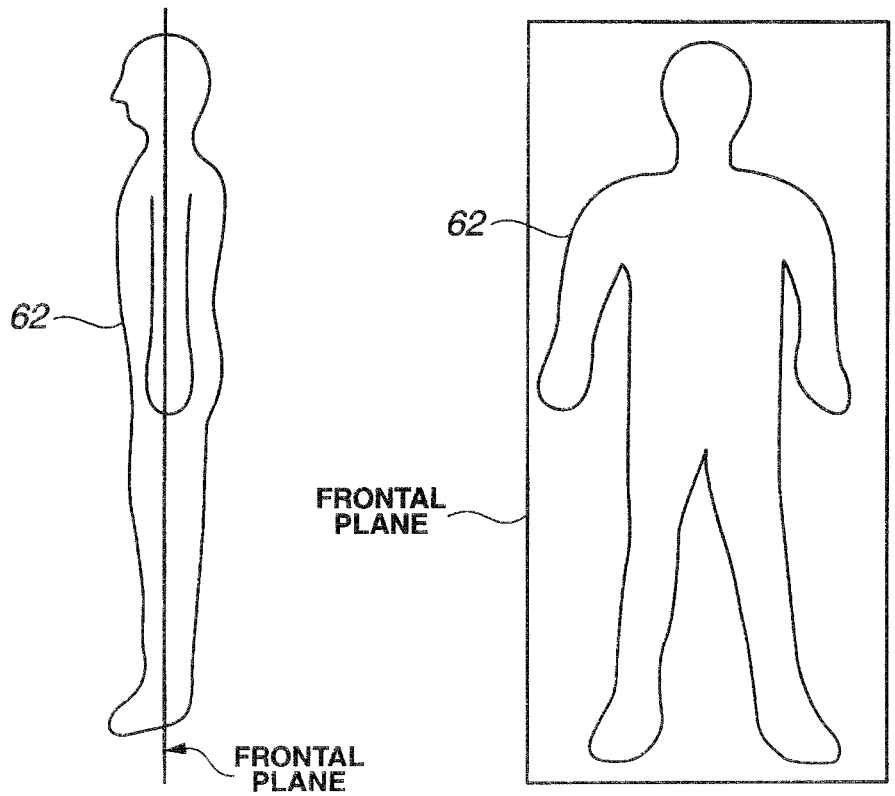
FIG. 3 is a diagram showing characteristic information stored in a characteristic information storing section in a table.
FIG. 4 is a view showing a frontal plane.

The plane is parallel with a frontal plane of the patient 62, and therefore, the source coil position calculation circuit 46 has a function of body position detection means which detects the body position of the patient 62 and also has a function of a frontal plane direction detection section 46a which detects a direction in which the frontal plane of the patient 62 is present (also called the direction of the frontal plane) In this case, the frontal plane means a plane which cuts the body of the patient 62 anteroposteriorly, and is shown in the view at the left side in FIG. 4.

The present embodiment adopts the configuration in which the direction of the frontal plane can be detected by using the patient plate 40, but may have the configuration in which a user such as a surgeon inputs the information for identifying the direction of the frontal plane in the bending control section 5 by input means such as a keyboard not illustrated.

The information of the patient plate 40 which is detected by the source coil position calculation circuit 46 is sent to the bending control section 5. The bending control section 5 has a function of a direction detection section 5b which detects the direction of the frontal plane with respect to the distal end side portion or the bending portion 16 of the insertion portion 11 from the information of the frontal plane of the patient 62, the positional information of the distal end portion 15 and the bending coordinates information of the bending portion 16.

In this case, the distal end side portion of the insertion portion 11 is constituted of the distal end portion 15, and the bending portion 16 which is formed adjacently to the rear end of the distal end portion 15 and is formed to be longer than the distal end portion 15, and therefore, the bending portion 16 can be regarded as a main part of the distal end side portion of the insertion portion 11.

In other words, the direction detection section 5b of the bending control section 5 detects an angle formed by the frontal plane with respect to the bending portion 16 at the distal end portion side of the insertion portion 11.

One of the source coils is set in the vicinity of, for example, an anus which is an insertion opening into a body cavity for the insertion portion 11, and thereby, can be used for detection of an insertion length of the insertion portion 11 which is inserted from the anus. More specifically, the insertion length of the insertion portion 11 can be detected from the positional information of the source coil 41 which is disposed in the insertion portion 11 which is at an inner side of the body cavity from the position of the anus by the source coil, or the insertion form.

Further, even though such a source coil is not used, the coordinates position of the source coil which is disposed at the distal end portion 15 at the time when the distal end portion 15 is set in the vicinity of the anus is stored, and thereby, the insertion length also can be detected from the detection information by the insertion form detection apparatus 8. More specifically, with use of only the detection information by the insertion form detection apparatus 8, the insertion length can be detected, and the position of the distal end portion 15 in the body cavity also can be detected.

Further, insertion length detection means with an encoder provided at a rotating shaft of a roller which is in contact with an outer peripheral surface of the insertion portion 11 may be disposed in the vicinity of an anus, and the insertion portion length may be detected from the detection signal from the encoder.

Further, in the present embodiment, a reference information storage section 61a which stores characteristic information or the like as the characteristics of each tube cavity site (also simply called a site) in various hollow organs in the shapes of tube cavities such as a large intestine in the body cavity into which the endoscope 2 is inserted, as reference information, is provided in a storage section 61.

The storage section 61 is configured by, for example, a nonvolatile memory such as a flash memory, a hard disk, or the like, is connected to the bending control section 5, and the bending control section 5 can add information to and update the reference information as well as refer to the reference information. The storage section 61 may be provided inside the bending control section 5.

The bending control section 5 refers to the characteristic information and the like of the tube cavity site around the position of the distal end portion 15 in the body cavity if the dark part disappears, and a shift to the search mode or a search instruction is made to search for the insertion direction, when the insertion portion 11 is inserted into a hollow organ such as a large intestine.

Subsequently, the bending control section 5 searches for the insertion direction (namely, the dark part) by using the search method suitable for the tube cavity site, and gives support to perform insertion into the body cavity smoothly.

Further, the bending control section 5 stores the information of the bending coordinates position (also called bend coordinates) as the bend coordinates information of the distal end side of the insertion portion 11 in the storage section 61 at the time of the operation of the insertion manipulation as will be described later. Accordingly, the storage section 61 is provided with a bend coordinates information storage section 61*b* which stores the past bend coordinates information including the present bend coordinates information. The storage section 61 is also provided with a program storage section 61*c* which stores the control program in the case of the bending control section 5 performing search processing. The control bending section 5 performs search processing and the like in accordance with the control program.

FIG. 3 shows a specific example of characteristic information in the case of, for example, a large intestine as a hollow organ in the shape of a tube cavity. The information of the medical characteristics of whether it is fixed or not, whether it is a substantially linear or not, and whether it is along the frontal plane or not is checked in advance with respect to respective tube cavity sites of a rectum, a sigmoid colon, a descending colon, a splenic flexure, a transverse colon, a hepatic flexure, and an ascending colon in the large intestine, and is stored in the reference information storage section 61*a* of the storage section 61.

For example, with respect to the characteristics of whether the rectum is (entirely) fixed or not, whether the rectum is substantially linear or not, and whether the rectum is along the frontal plane or not, a circle is given since the rectum is fixed, a cross is given since the rectum is not substantially linear, and a circle is given since the rectum is along the frontal plane.

Further, with respect to the characteristics of whether the sigmoid colon is fixed or not, whether the sigmoid colon is substantially linear, and whether the sigmoid colon is along the frontal plane or not, a cross is given since the sigmoid colon is not fixed, a cross is given since the sigmoid colon is not substantially linear, and a triangle is given since the sigmoid colon is not entirely along (only partially along) the frontal plane.

Further, the reference information storage section 61*a* stores search methods suitable for tube cavity sites from a plurality of search methods (the first search method and the second search method) in preparation for the case of requiring search (for the insertion direction since a dark part disappears) in the state in which the distal end portion 15 is located at the respective tube cavity sites.

In the case of searching for the insertion direction, the bending control section 5 selects the search method stored in the reference information storage section 61*a* to perform search processing. More specifically, the bending control section 5 has a function of a selection section 5*c* which automatically selects the search method suitable for the tube cavity site from a plurality of search methods.

As above, in the present embodiment, when a dark part disappears at the time of insertion manipulation, the mode shifts to the search mode of performing search processing in accordance with the reference information of the medical characteristics and the like shown in FIG. 3. When the dark part disappears, a suitable search method is adopted in accordance with the characteristic of the tube cavity site around the position of the distal end portion 15 in the case of disappearance of the dark part, from a plurality of search methods which are prepared in advance.

In a broad sense, when a dark part disappears, based on the position in the body cavity, of the distal end portion 15 of the insertion portion 11, which is detected by the position detection section 5*a*, the selection section 5*c* selects a suitable search method corresponding to the aforesaid position from a plurality of search methods which are prepared in advance for searching for the bending direction of the bending portion 16.

The tube cavity site around the position of the distal end portion 15 in the body cavity can be identified with high precision by using the insertion length, besides the information of the insertion form by the insertion form detection apparatus 8 and the positional information of the distal end portion 15.

FIG. 3 shows the insertion lengths from the anus as the insertion opening to the rectum, the sigmoid colon, . . . , to the ascending colon by La, Lb, . . . , and Lg, and the tube cavity site around the position which the distal end portion 15 reaches can be identified from these insertion lengths. From the reference information shown in FIG. 3, the search method suitable for each of the identified tube cavity sites can be determined. Accordingly, the reference information also becomes the identification information for identifying the tube cavity site around a position from the position in the body cavity of the distal end portion 15 detected by the position detection section 5*a*. Further, the reference information storage section 61*a* also has a function of the information storage section which stores the identification information.

The bending control section 5 has a function of a bending direction determination section 5*d* as bending direction determining means which determines the bending direction in which the bending portion 16 is bent by the selected search method. FIG. 4 shows an explanatory view of the frontal plane.

The plane which cuts the body of the patient 62 anteroposteriorly shown at the left side of FIG. 4 is the frontal plane, and the frontal plane has the same meaning as a side section. The frontal plane is the plane perpendicular to the plane which cuts the body laterally symmetrically, or a sagittal plane as a plane parallel with the plane which cuts the body laterally symmetrically.

Figure 5:
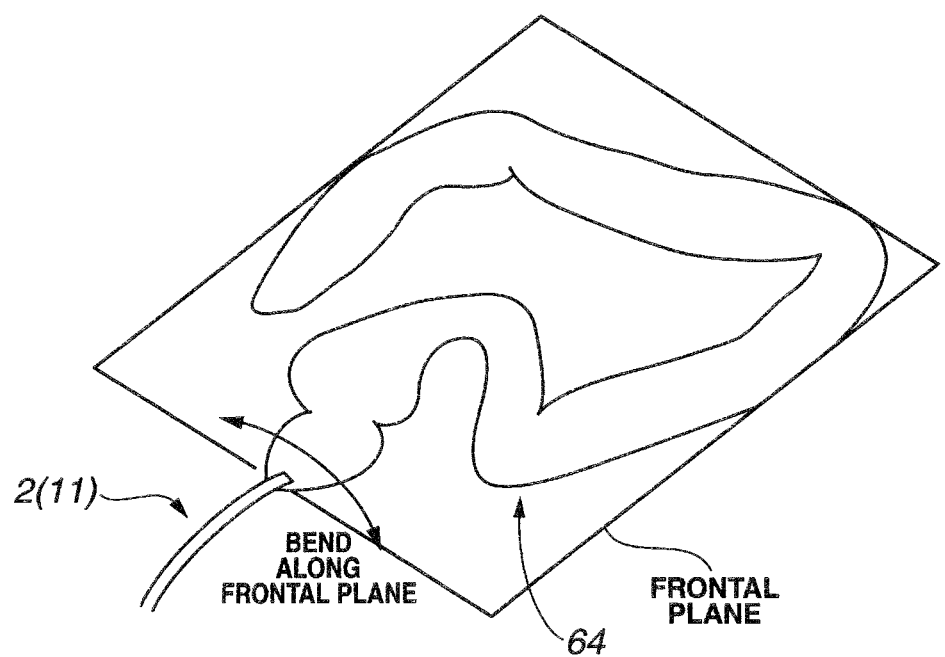
FIG. 5 is a view showing a state of inserting an insertion portion of the endoscope into a large intestine.

The right side of FIG. 4 shows the state of the case of the patient 62 who is lying on his or her back (may be lying on his or her stomach). When the patient 62 lies on his or her back like this, the rectum and the like shown in FIG. 3 are at the positions along the frontal plane. Accordingly, when the patient 62 is set in the state of lying on his or her back as shown in FIG. 5, when the insertion portion 11 is inserted into, for example, a rectum inside the large intestine 64, if the bending portion 16 at the distal end side of the insertion portion 11 is bent along the frontal plane, insertion to the deep portion side can be smoothly performed, since the rectum is located along the frontal plane.

In the case of the tube cavity site along the frontal plane like this, search for the insertion direction is performed along the frontal plane by using the characteristic of it, whereby insertion can be performed more smoothly than the case without using the characteristic.

As will be described later with FIGS. 8 and 9, in the case of adoption of the first search method, the direction detection section 5*b* of the bending control section 5 detects the direction of the frontal plane in the bending portion 16 from the information of the frontal plane in the patient 62 and the bending information at the distal end side of the insertion portion 11, and searches for the insertion direction along the frontal plane.

On the other hand, in the case of the tube cavity site like the sigmoid colon which is not entirely along the frontal plane, the second search method differing from the first search method is selected and used. In this case, as will be described later with FIGS. 10 and 11, the past bending position information is referred to, and the bending direction is determined so as to bend the bending portion 16 in the direction in which the bending portion 16 is not bent in the past, whereby the insertion direction is searched for.

As above, in the present embodiment, a plurality of search methods corresponding to the characteristics of the tube cavity sites where the distal end portion 15 is located, which need search, are prepared in advance for the case in which the insertion portion 11 is inserted into a hollow organ such as the large intestine 64 in the body cavity into which the insertion portion 11 is inserted, the dark part disappears, and search is needed, so that the suitable search method is selected and used in accordance with the characteristic of the tube cavity site and smooth insertion can be supported.

Figure 6:
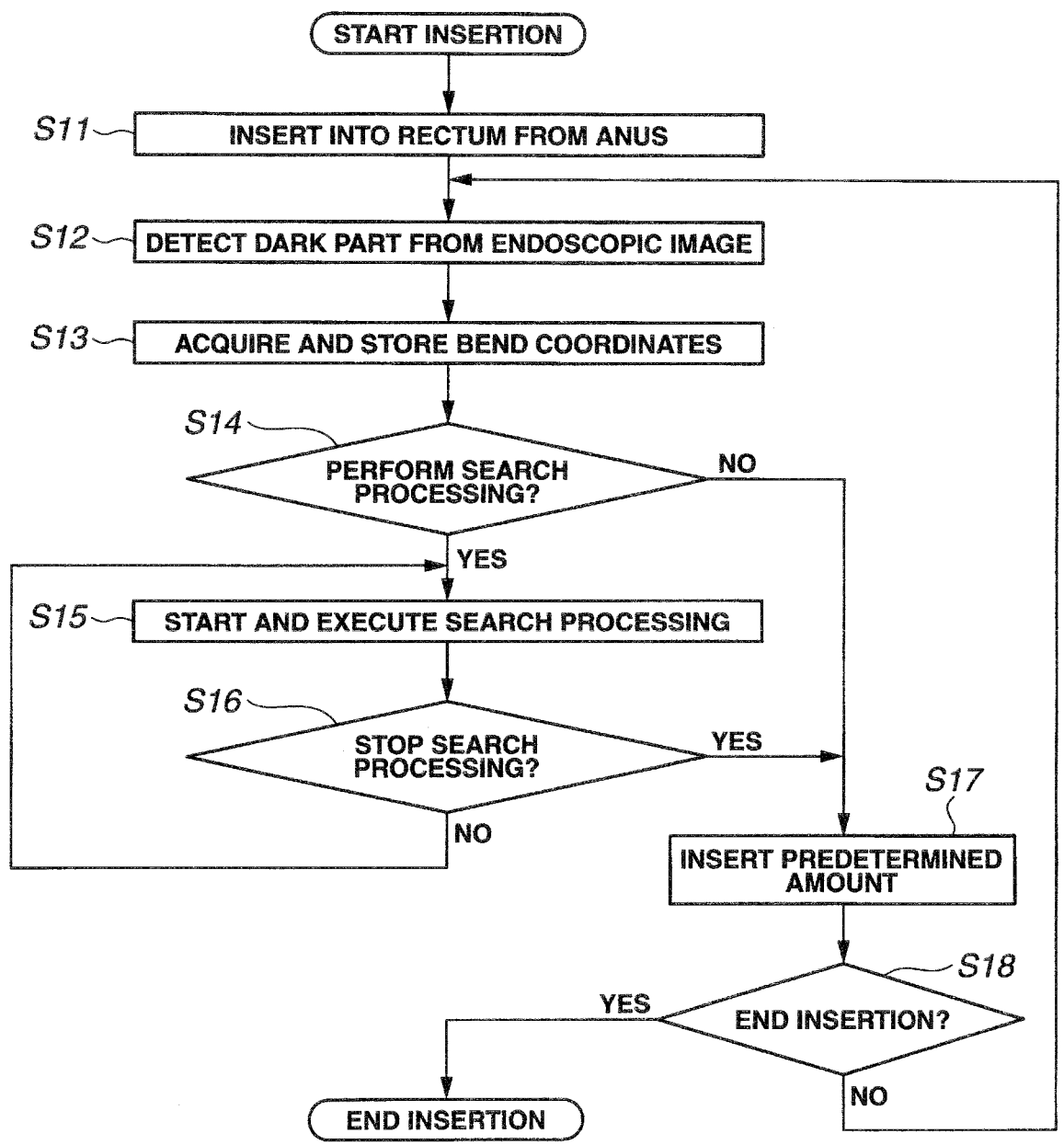
FIG. 6 is a flowchart showing a procedure in the case of inserting the insertion portion of the endoscope into a large intestine.

Next, an operation according to the present embodiment will be described with reference to a flowchart of FIG. 6. As shown in FIG. 1, the connector 14 of the endoscope 2 is connected to the video processor 6, the insertion form detection apparatus 8 is connected to the video processor 6, and the power supply is turned on, so that the video processor 6 and the insertion form detection apparatus 8 are set to the operation state.

Further, the position of the distal end portion 15 with the distal end portion 15 placed in the vicinity of an anus as described above is stored as described above, and thereby, the insertion length of the insertion portion 11 into the large intestine thereafter also can be detected. In the following, the description is made on the assumption that the mode is set at an automatic insertion mode, for example.

In this case, the bending control section 5 determines the bending direction of the bending portion 16 so that the dark part in the endoscopic image is the target position of the insertion direction, and the electric motors 55a and 55b which configure the bending drive means bend and drive the bending portion 16 in the determined direction. Subsequently, a surgeon grips the proximal end side of the insertion portion 11 to perform an operation of pushing the distal end side of the insertion portion 11 into the large intestine.

As shown in step S11, the surgeon inserts the distal end portion 15 of the insertion portion 11 of the endoscope 2 into a rectum from an anus for performing endoscopy of the inside of, for example, the large intestine of the patient 62.

When the surgeon inserts the distal end portion 15 of the insertion portion 11 into the deep part side of the rectum, the dark part detection circuit 37a of the video processing circuit 37 detects the dark part by image processing from the endoscopic image picked up by the image pickup unit 31 as shown in step S12, and sends the detection result of presence or absence of the dark part to the bending control section 5.

Further, in step S13, the bending control section 5 acquires the bend coordinates of the bending portion 16 at the distal end side of the insertion portion 11 at each image pickup period (period differing from this may be adopted) of the image pickup unit 31, for example, and stores the bend coordinates in the storage section 61. In this manner, in synchronism with the operation of inserting the distal end side of the insertion portion 11 into the deep part side of the large intestine 64, processing of dark part detection of step S12 and processing of acquisition of the bend coordinates of step S13 are performed.

The information which is stored by the processing of step S13 is used in the case of adoption of the second search method which will be described later, and the details of it will be described later with FIG. 10.

Further, as shown in the next step S14, the bending control section 5 determines whether or not to perform search processing in accordance with the presence, absence or the like of the dark part by step S12.

When the image of the dark part is not detected from the endoscopic image, and the insertion direction cannot be determined, the bending control section 5 starts and executes search processing as shown in step S15. In the next step S16, the bending control section 5 determines whether to stop the search processing.

In accordance with the tube cavity site where the distal end portion 15 is located, the search processing suitable for the tube cavity site is performed, and thereby, the state is highly likely to be set to the state of being capable of smoothly detecting the dark part. When the dark part is detected by the dark part detection circuit 37a, the bending control section 5 performs determination of stopping the search processing. When the surgeon performs an instruction operation of stopping the search processing, the bending control section 5 also performs determination of stopping the search processing.

In the case of the determination result of not stopping the search processing in step S16, the flow returns to the processing of step S15, and the search processing is continued.

When the search processing is not performed in step S14, and when the search processing is stopped in step S16, the flow proceeds to the processing of step S17, and in step S17, the bending control section 5 waits until the insertion portion 11 is inserted by a predetermined small amount from the previous state by the surgeon. For example, the bending control section 5 performs the processing of step S17 by using detection of the insertion length. The flow may proceed to step S18 without performing the processing of step S17.

After step S17, the bending control section 5 performs determination of whether the insertion ends in step S18. When the surgeon performs insertion to the final insertion target position or insertion target site of the ascending colon or the like in the large intestine, for example, the surgeon performs an instruction operation of end of insertion, and performs endoscopy while observing the endoscopic image as the surgeon performs an operation of extracting the insertion portion 11.

The surgeon may set the target insertion length and gives the target insertion length to the bending control section 5 in advance, and when the detected insertion length reaches the target insertion length, the bending control section 5 may end automatic insertion.

When the instruction operation of ending the insertion is not performed, the flow returns to the processing of step S12, and the same operation is repeated. Meanwhile, when the instruction operation of ending the insertion is performed, the control operation of FIG. 6 is ended. When the search processing of step S15 in FIG. 6 is started, and the search method of the search processing is executed, from the position of the distal end portion 15 of the insertion portion 11 in the large intestine at the time point when the search processing is started, the tube cavity site which the position reaches is detected (identified).

For detection of the tube cavity site according to the position which the distal end portion 15 reaches, the insertion length (of the insertion portion 11) into the body cavity can be used.

Figure 10:
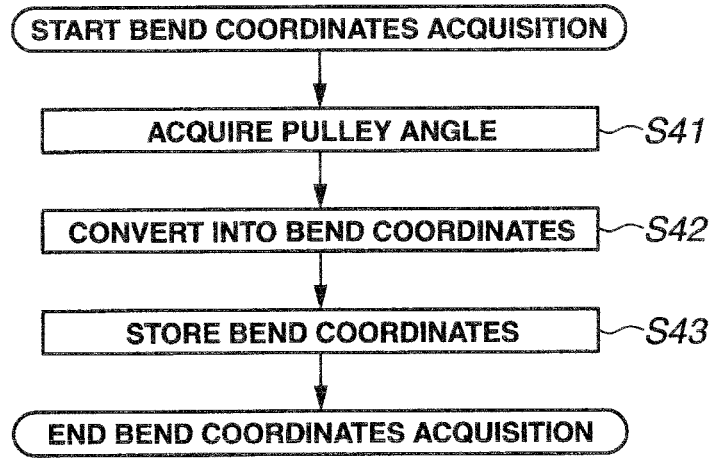
FIG. 10 is a flowchart showing a procedure of acquisition of bend coordinates.

In order to detect the tube cavity site at the position which the distal end portion 15 reaches with higher precision, detection may be performed in accordance with the method described in the flowchart of FIG. 10 of Japanese Patent Application No. 2008-259882 by the present inventor.

In Japanese Patent Application No. 2008-259882, the position of the distal end portion 15 is detected from at least two values of the insertion length, the direction angle which the distal end portion 15 faces, the bending amount, the bending direction angle, and the insertion portion radius of curvature maximum value. By using the information of a plane or the like parallel with a bed surface with respect to the patient in the state lying on his or her back on the bed, the tube cavity site as the site in the body cavity at the position which the distal end portion 15 reaches is detected (identified).

Next, the search processing of step S15 of FIG. 6 will be described according to a flowchart of FIG. 7A.

When starting the search processing, the bending control section 5 acquires the information of the insertion form of the endoscope 2 from the insertion form detection apparatus 8 in the first step S21. In this case, the bending control section 5 acquires the information of the position of the distal end portion 15, the distal end portion direction as the longitudinal direction of the distal end portion and the upper direction of the CCD 33 (the upper direction of the bend of the bending portion 16) from the positional information of a plurality of source coils 41 disposed in the distal end portion 15 from the source coil position calculation circuit 46 in the insertion form detection apparatus 8, for example.

In the next step S22, the bending control section 5 acquires the information of the bend coordinates. More specifically, the bending control section 5 acquires the pulley angles corresponding to the present bending angle of the bending portion 16 from the encoders 57a and 57b.

Subsequently, in the next step S23, the bending control section 5 selects a search method. Selection of the search method will be described in accordance with FIG. 7B. When the search method is started, the bending control section 5 identifies the tube cavity site where the distal end portion 15 is located at the time of start of the search from the insertion length, for example, as shown in step S27.

Subsequently, in the next step S28, in accordance with the tube cavity sites shown in FIG. 3, the bending control section 5 selects the search method suitable for the tube cavity site from the first search method and the second search method. More specifically, the bending control section 5 selects the first or the second search method as the search method suitable for the characteristic of the tube cavity site where the distal end portion 15 is located when the dark part disappears and search is started, as shown in FIG. 3.

Figure 7A:
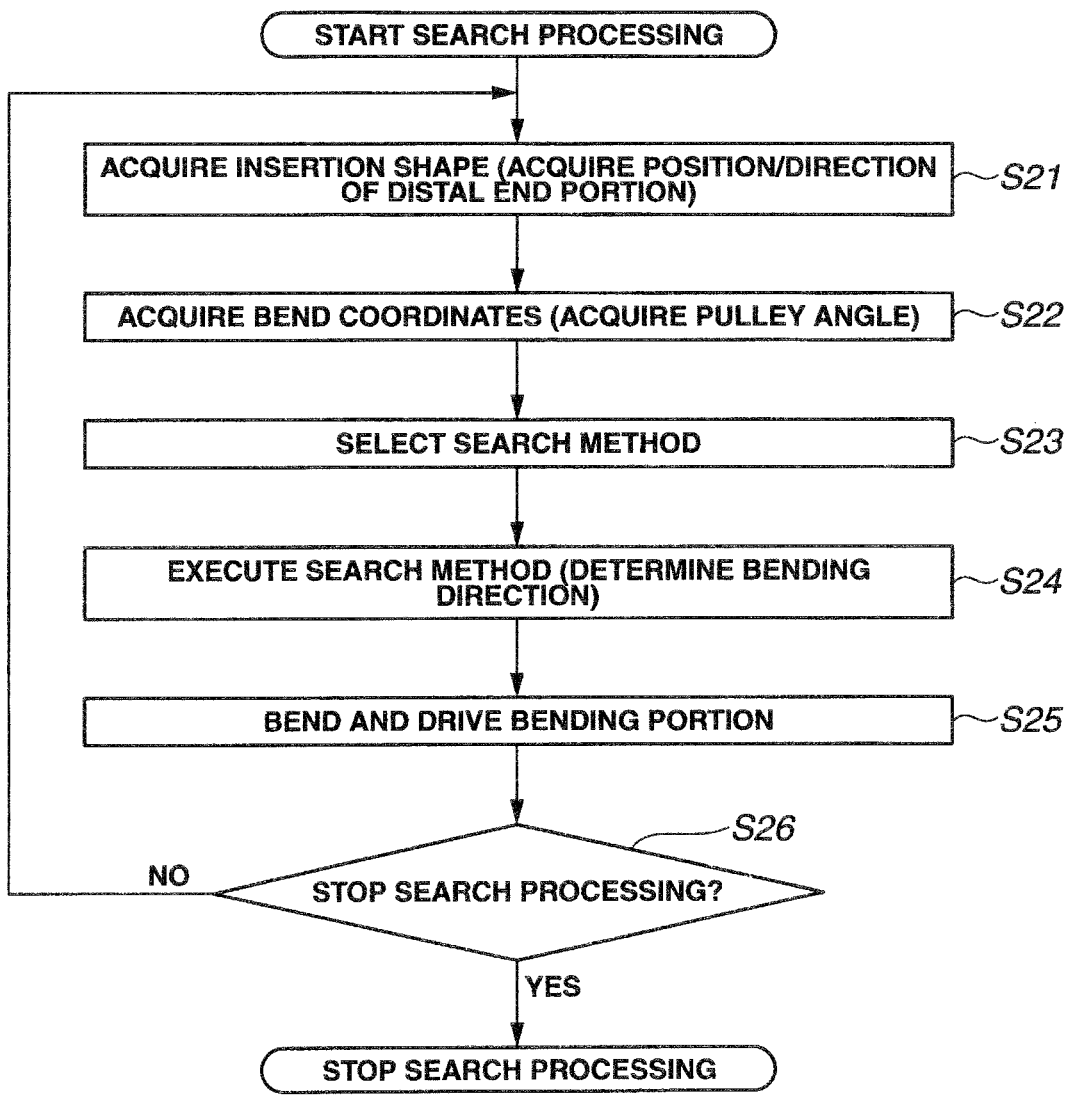
FIG. 7A is a flowchart showing a procedure of search processing in FIG. 6.
Figure 7B:
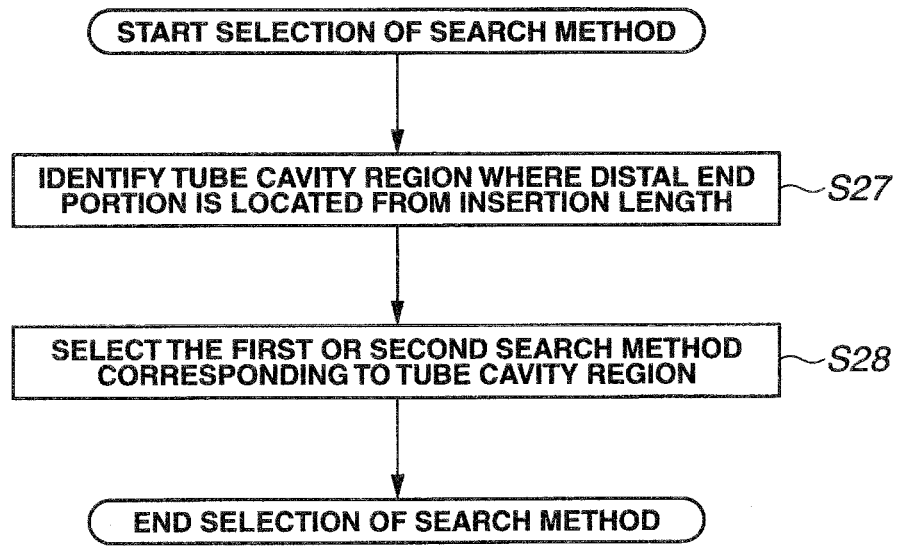
FIG. 7B is a flowchart showing a procedure of selecting a search method.

The selection processing of the search method of FIG. 7B ends as above, and the flow proceeds to the processing of step S24 of FIG. 7A. In step S24, the bending control section 5 executes the selected search method (more specifically, the first search method or the second search method). The bending direction determination section 5d of the bending control section 5 determines the bending direction in which the bending portion 16 is bent in accordance with the selected search method.

The processing of determining the bending direction will be described later with FIGS. 8 and 10. Subsequently, the bending control section 5 outputs the control signal for driving the bending portion 16 in the determined bending direction to the motor drive section 56. As shown in step S25, the motor drive section 56 bends and drives the bending portion 16 in the bending direction determined according to step S24 via the electric motors 55a and 55b as the bending drive means.

In the next step S26, the bending control section 5 performs determination of whether or not the search processing corresponds to the condition of stop. When the search processing does not correspond to the condition, the flow returns to the processing of step S21, and when the search processing corresponds to the condition, the bending control section 5 stops the search processing and ends the processing of FIG. 7A, and performs the processing of step S17 of FIG. 6.

Next, the search method selected by selection of the search method in step S23 of FIG. 7A, or the first search method or the second search method which is selected according to step S28 of FIG. 7B will be described more specifically.

Figure 8:
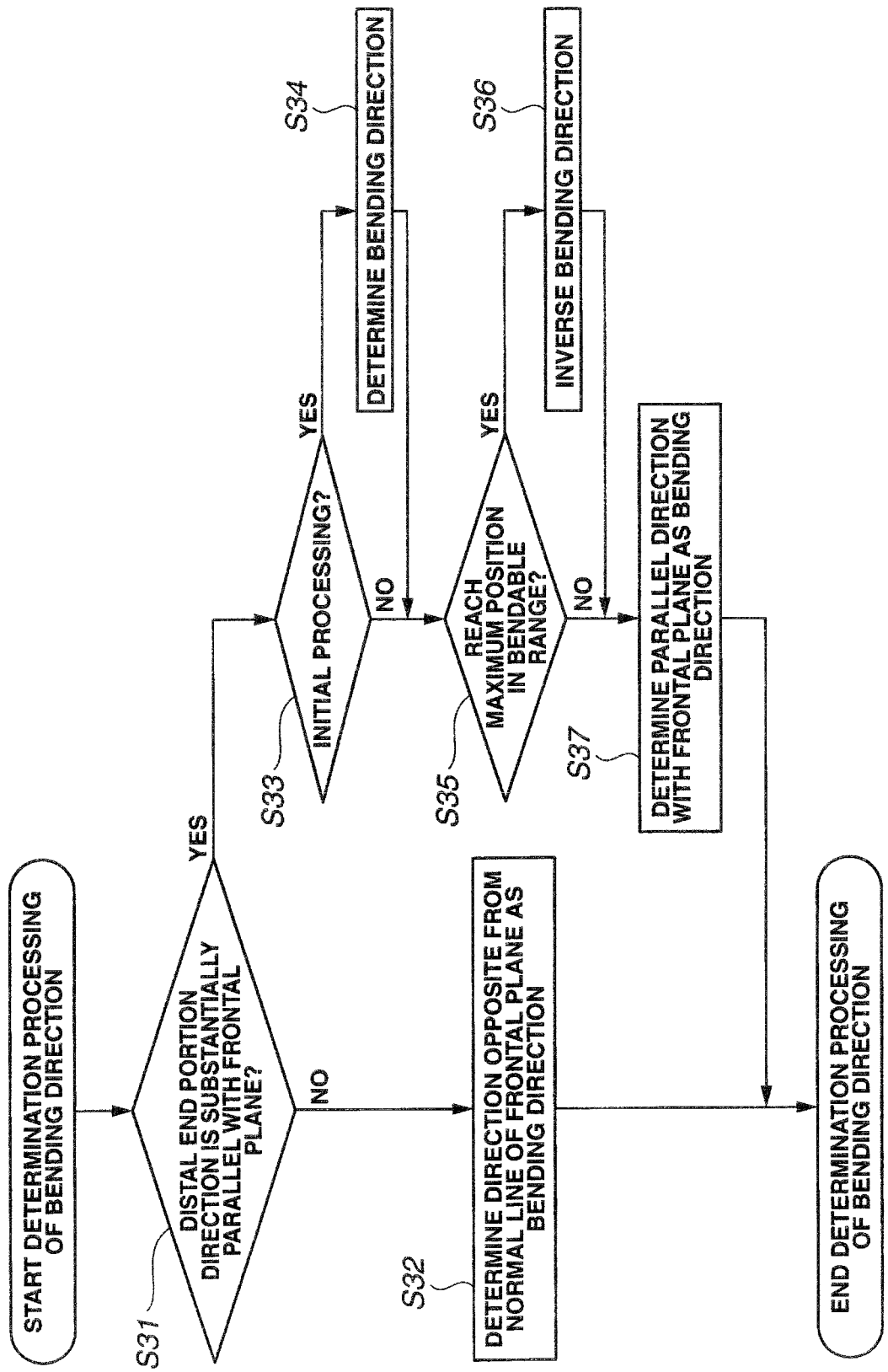
FIG. 8 is a flowchart showing a procedure of determination processing of a bending direction in the case of selecting a first search method in FIG. 7B.

FIG. 8 shows a control procedure of determining the bending direction when the first search method is selected by step S28 of FIG. 7B. In the first search method described with FIG. 8, (the search method is such that) the bending direction is determined so that the bending portion 16 at the distal end side of the insertion portion 11 is bent along the plane substantially parallel with the frontal plane.

When the determination processing of the bending direction in the case of the first search method is started, the bending control section 5 performs determination of whether or not the distal end portion direction (at the distal end side of the bending portion 16) is substantially parallel with the frontal plane in the first step S31 shown in FIG. 8. The direction detection section 5b of the bending control section 5 performs the determination by using the information of the frontal plane and the information of steps S21 and S22 of FIG. 7A.

The above described distal end portion direction is the direction which is the forward side along the longitudinal direction of the distal end portion 15 of the insertion portion 11 (shown by a vector V in FIG. 9(A)), and the plane including the distal end portion direction can be regarded as a plane including the distal end side of the bending portion 16.

The bending control section 5 performs determination of whether or not the distal end portion direction is substantially parallel with the frontal plane, more specifically, is parallel within ±10°.

Figure 9:
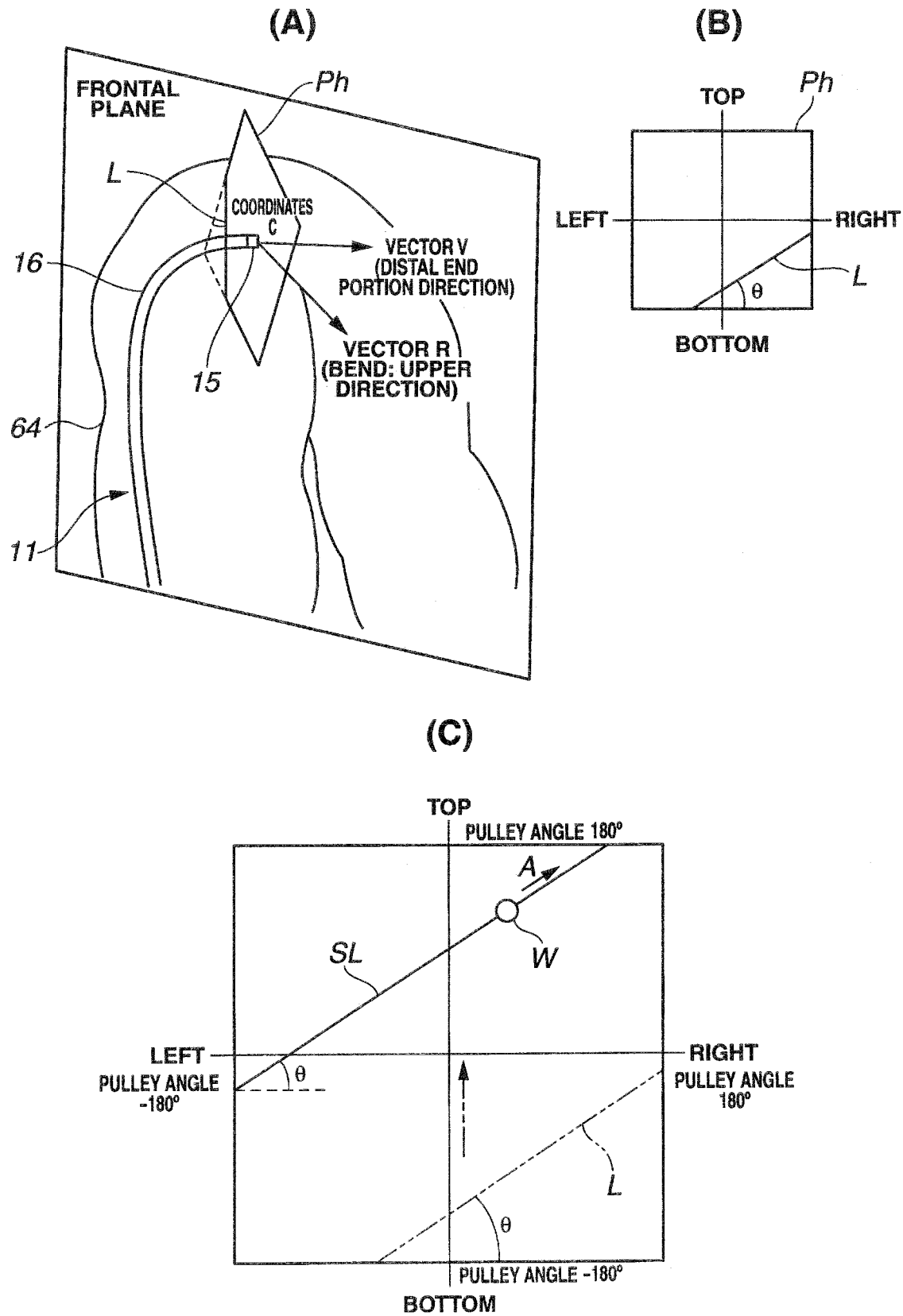
FIG. 9 is an explanatory diagram in FIG. 8.

According to step S21 which is used for performing the determination of step S31, the information of the coordinates (position) C (Cx, Cy, Cz) of the distal end portion 15, the distal end portion direction V (Vx, Vy, Vz) and an upper direction R (Rx, R, Rz) of the CCD 33 is acquired as shown in FIG. 9 (A). In this case, for example, (Cx, Cy, Cz) represents the X, Y and Z components of the coordinates C.

In a spine position, in the case of the coordinate system in which the upper direction of the bed on which the patient 62 is placed in a spine position is set as a Z-direction, the normal line direction of the frontal plane is (0, 0, 1).

When the distal end portion 15 and the bending portion 16 which correspond to the distal end side portion of the insertion portion 11 lie on the frontal plane, the angle formed by the distal end portion direction at the distal end side of the bending portion 16 and the normal line of the frontal plane is 90°. The angle formed by the frontal plane and the distal end portion direction is generally 90-(the angle formed by the distal end portion direction and the normal line of the frontal plane).

When the formed angle is within ±10°, that is, the distal end portion direction satisfies the condition of being substantially parallel with the frontal plane, the bending control section 5 determines that the bending portion 16 is on the frontal plane.

When the distal end portion direction does not satisfy the condition, the flow proceeds to step S32, and in step S32, the bending control section 5 determines the bending direction so as to set the direction opposite from the normal line of the frontal plane as the drive direction, and ends the processing of FIG. 8.

On the other hand, in the case of the determination result that the distal end portion direction is substantially parallel with the frontal plane in step S31, the flow proceeds to step S33. In this case, the bending control section 5 determines the bending direction to bend the bending portion 16 while the bending portion 16 keeps the state substantially parallel with the frontal plane.

FIG. 9 (A) three-dimensionally shows the state of the distal end side of the insertion portion 11 which is inserted into the large intestine 64 in the case of the determination result that the distal end portion direction is substantially parallel with the frontal plane. An intestine tract of the large intestine 64 is substantially parallel with the frontal plane, and the distal end side of the insertion portion 11 is also substantially parallel with the frontal plane.

In order to determine the bending direction, the bending control section 5 temporarily sets a phantom plane Ph with the distal end portion direction (vector V) set as the normal line direction at the position (the coordinates C) of the distal end portion 15 on FIG. 9 (A), and obtains an intersection line L of the phantom plane Ph and the frontal plane. Further, in FIG. 9 (A), the upper direction of the bend (more specifically, the upper direction of the CCD 33) is shown by the vector R.

Further, the bending control section 5 calculates a rotational angle θ with respect to the lateral direction of the bend, of the intersection line L with the frontal plane in the phantom plane Ph as shown in FIG. 9 (B). FIG. 9 (B) shows the state in which the upper direction corresponds to the upper direction of the bend (that is, the upper direction of the CCD 33).

Next, the bending control section 5 translates the intersection line L shown in FIG. 9(B) as shown by the arrow of the two dot chain line in FIG. 9(C), and sets a straight line SL to pass through a present bend position W shown by a pulley angle as shown in FIG. 9(C).

Subsequently, the bending control section 5 determines the bending direction to move toward the end point of the straight line with a shorter distance from the present bent position W to the end point of the straight line SL. In the case of FIG. 9 (C), the bending direction is the direction shown by the arrow A. Further, when the distal end portion 15 reaches the end portion, that is, reaches the maximum position in the bendable range, the bending method is determined so that the direction is inverted. In this manner, the bending direction is sequentially determined to be in the direction along the frontal plane.

The determination procedure in this case corresponds to steps S33 to S37 of FIG. 8.

In step S33, the bending control section 5 determines whether or not it is the initial (bending direction determination) processing. When determining that it is the initial processing, the bending control section 5 determines the bending direction to move along the straight line SL from the present bent position W in the upper right direction (direction close to the maximum position in the bendable range) shown by the arrow A as shown in FIG. 9(C) to be the bending direction of the bending portion 16 (step S34).

After step S34, the flow proceeds to step S35. Further, when it is not determined as the initial processing in step S33, the flow proceeds to step S35, and the bending control section 5 determines whether the bending portion 16 reaches the maximum position in the bendable range in step S35.

The case of FIG. 9(C) corresponds to the determination of whether or not the bending portion 16 reaches the end portion (the maximum position in the bendable range) at the upper right side of the straight line SL. When it is not the case corresponding to the determination of step S35, the parallel direction with the frontal plane is determined as the bending direction (drive direction) as shown in step 37, and the processing of FIG. 8 is ended.

On the other hand, when it is the case corresponding to the determination of step S35, the bending direction is inverted as shown in step S36, and the flow proceeds to the processing of step S37.

In the first search method, the determination processing of the bending direction is thus performed. More specifically, by using the characteristic that the tube cavity site is along the frontal plane, the bending direction is determined so that the bending portion 16 is bent and driven along the frontal plane, whereby search for the insertion direction when the dark part disappears can be smoothly performed.

Next, with reference to FIGS. 10 and 11, the second search method will be described. The second search method is for searching for the direction in which bending is not performed (namely, observation is not performed) in the past. In other words, the second search method is (a searching method) for searching for the insertion direction by performing bending in the bending direction in which bending is not performed in the past with reference to the past bending history.

Therefore, acquisition processing of bend coordinates of FIG. 10 is performed first. When the acquisition processing of the bending coordinates is started, the bending control section 5 acquires the pulley angles of the pulleys 54a and 54b via the encoders 57a and 57b in the first step S41.

In the next step S42, the bending control section 5 performs conversion of the bend coordinates from the pulley angles. Conversion of the bend coordinates means linearization of the relationship of the pulley angle and the bend coordinates, and conversion is performed by using the correspondence table (map) of the pulley angles and the bend coordinates, for example.

In the next step S43, the bending control section 5 stores the converted bend coordinates in the bend coordinates information storage section 61b of the storage section 61 as bend coordinates information. Subsequently, the bending control section 5 ends acquisition processing of the bend coordinates of FIG. 10.

Figure 11:
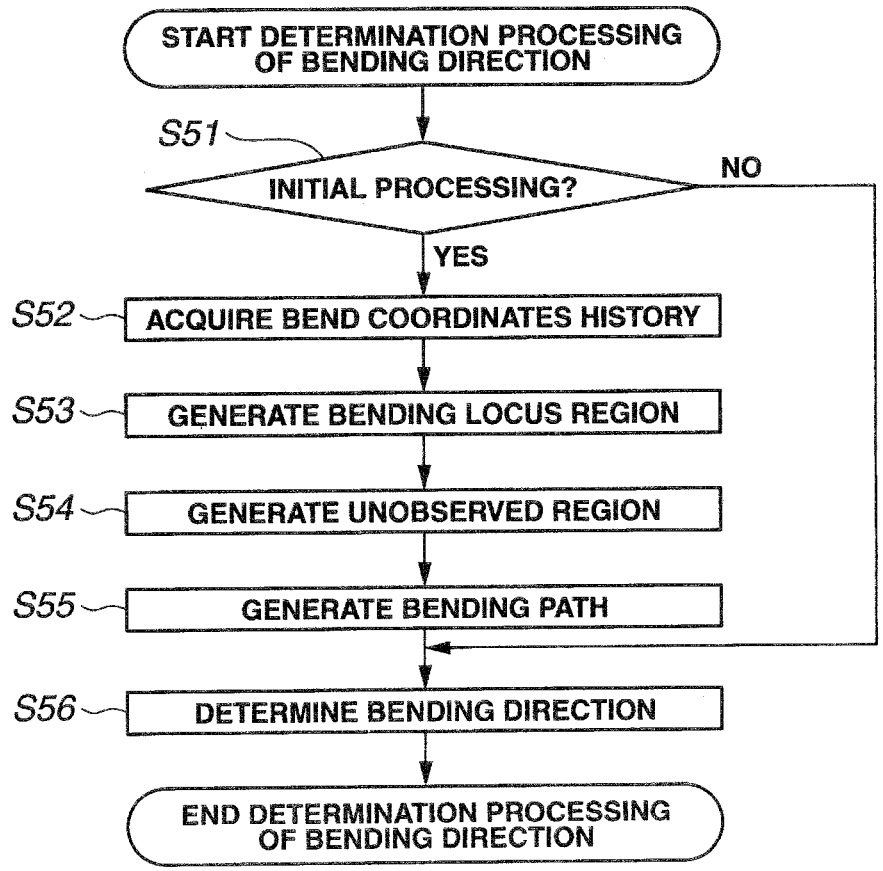
FIG. 11 is a flowchart showing a procedure of determination processing of a bending direction in the case of selecting a second search method in FIG. 7B.

Next, the determination processing of the bending direction shown in FIG. 11 is started.

In the first step S51, the bending control section 5 determines whether it is the initial processing. When it is the initial processing, the flow proceeds to step S52, and the bending control section 5 performs setting of the bending path for determining the bending direction in step S52 and the following steps.

In step S52, the bending control section 5 acquires a bend coordinates history from the bend coordinates information storage section 61b. In step S52, the bending control section 5 acquires a plurality of past bend coordinates including those of the present as the information of the bend coordinates history.

Figure 12:
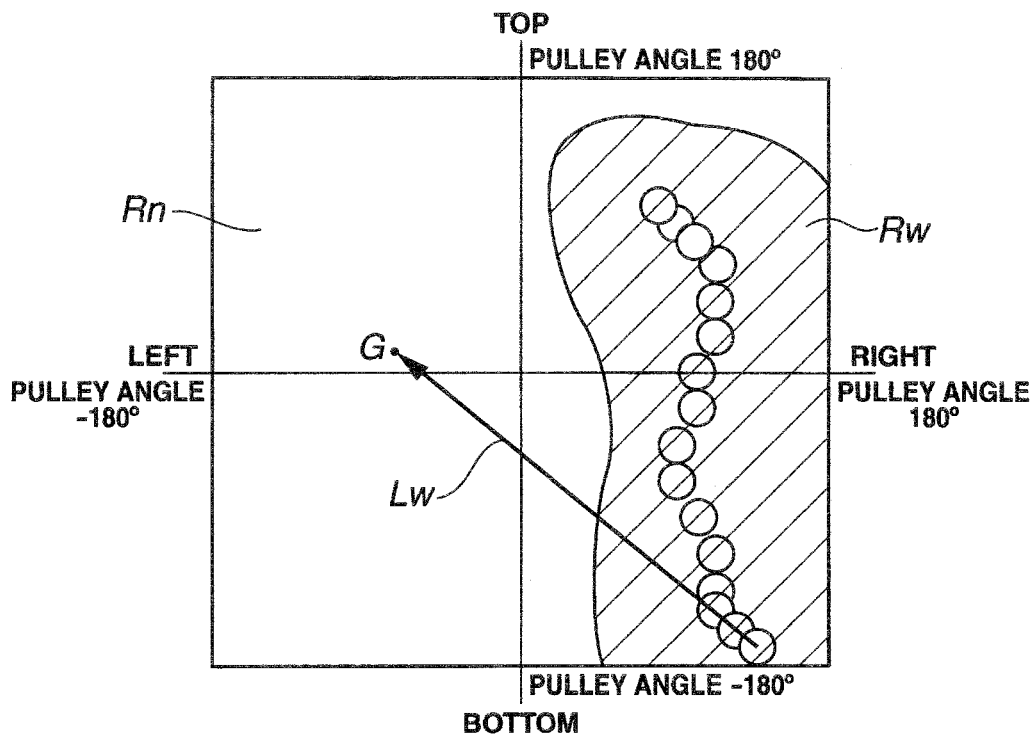
FIG. 12 is an explanatory diagram of processing of generating a bending path in FIG. 11.

In the next step S53, the bending control section 5 performs processing of generating a bending locus region from the information of a plurality of past bend coordinates which is acquired. FIG. 12 shows an explanatory diagram of a state of generating the bending locus region.

The bending control section 5 converts, for example, 16 bend coordinates of the past, which are acquired, into the coordinates of the pulley angles and expresses them by a polygonal line. What is expressed by a polygonal line is shown by white circles in FIG. 12.

Next, the bending control section 5 expands the polygonal line expressed by the polygonal line to a region by known expansion processing (for example, Morphology conversion processing), and generates a bending locus region Rw as shown by the oblique line of FIG. 12.

In the next step S54, the bending control section 5 generates an unobserved region Rn by using the bending locus region Rw. More specifically, the bending control section 5 generates the unobserved region Rn by subtracting the bending locus region Rw from the movable range of bend.

In the next step S55, the bending control section 5 generates a bending path from the unobserved region Rn. When generating the bending path, the bending control section 5 obtains a center of gravity G of the unobserved region Rn as shown in FIG. 12, and sets the center of gravity G as the bending path for determining the bending direction from the present bend coordinates.

In the next step S56, the bending control section 5 determines the bending direction from the present bend coordinates and the bending path. In the case of FIG. 12, the bending control section 5 determines the direction of a bending path Lw which connects the center of gravity G and the present bend coordinates as the bending direction. This case is an example in which the bending direction is uniquely determined from the bending path.

Figure 13:
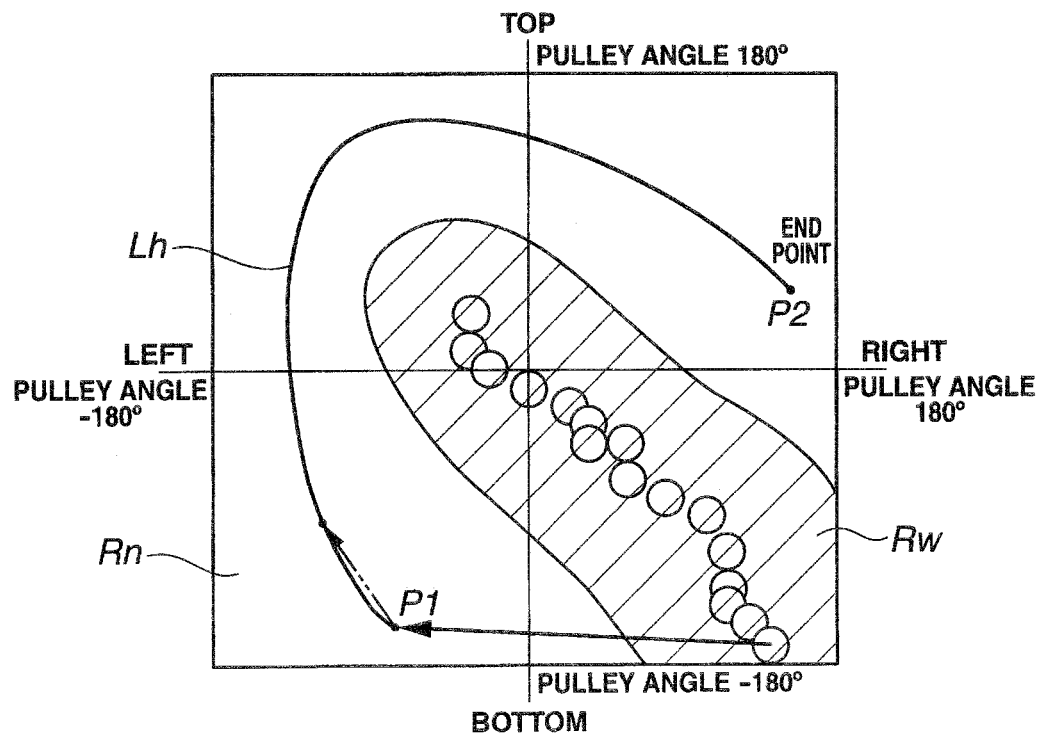
FIG. 13 is an explanatory diagram of processing of generating a bending path differing from FIG. 12.

When it is not determined as the initial processing in the determination processing of step S51, that is, when the bending path is already set (generated), the bending control section 5 determines the bending direction from the present bend coordinates and the bending path as described above. Subsequently, the bending control section 5 ends the determination processing of the bending direction shown in FIG. 11. As the method for generating the bending path in step S55, for example, a method shown in FIG. 13 which differs from the above description may be adopted. Further, the direction of FIG. 12 and the direction described with FIG. 13 and the like may be made selectable. FIG. 13 shows an explanatory diagram of one example of another method.

The case shown in FIG. 13 is the same as FIG. 12 in the processing up to generation of the unobserved region Rn of step S54. The bending control section 5 performs thinning for the unobserved region Rn according to a known method of Hilditch or the like. The bending control section 5 sets a line Lh which connects one end point P1 of a thin line generated by thinning and another end point (terminal end) P2 from the present bend coordinates, as the bending path.

In this case, in the bending direction determination processing of the next step S55, the direction toward the one end point P1 in the line Lh of the bending path, for example, from the present bend coordinates is determined to be the bending direction as shown in FIG. 13. Subsequently, the bending portion 16 is bent and driven in the determined bending direction.

The example shown in FIG. 13 shows the method for further covering the bending direction in which the bending portion is not bent, in addition to performing search in the bending direction in which the bending portion is not bent in the past by referring to the history of the past bend coordinates as in the case shown in FIG. 12. Describing more specifically, for example, in the initial processing, the direction shown by the thick arrow of FIG. 13 is determined as the bending direction.

Subsequently, the bending portion is bent and driven in the determined bending direction, and search for the insertion direction is performed. When the search processing is not ended, the second bending direction which differs from the first (first time) bending direction in the bending path within a moderate angle range is determined as shown by the arrow of the two dot chain line of FIG. 13, for example, and search processing is performed in the bending direction. When the insertion direction is not found in the second search processing, the determination processing of the third bending direction is performed, and at the third time, the bending direction is similarly determined by the processing of replacing the first time with the second time. The same thing applies to the fourth time and the following times.

When the search processing is not finished as above, the bending directions are determined so that the bending directions are covered along the bending path in which the bending portion is not bent in the past. Consequently, according to the method, the insertion direction can be reliably found while coverage is performed from the one end point P1 to the terminal point P2 on the bending path.

Figure 14:
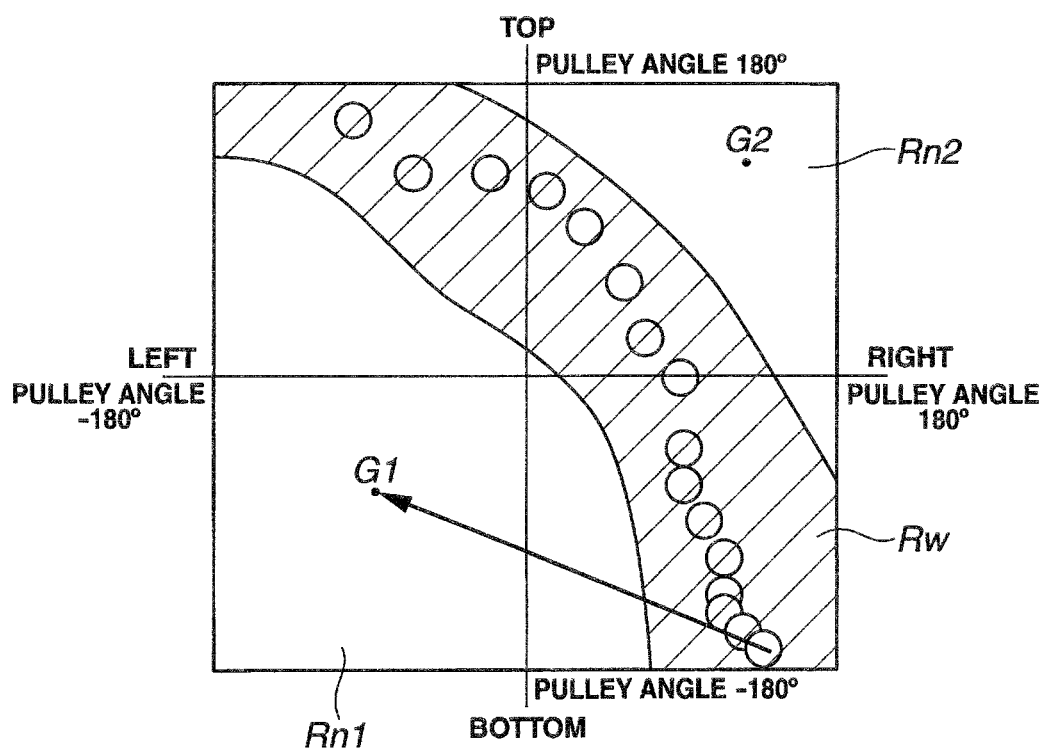
FIG. 14 is an explanatory diagram of setting a bending path for the case with two unobserved regions.

When the unobserved region Rn is generated by step S54, the two unobserved regions Rn1 and Rn2 are sometimes generated separately from each other as shown in FIG. 14.

In such a case, the line which connects the center of gravity G of the unobserved region with a larger area and the present bend coordinates is set as the bending path. Alternatively, the centers of gravity G1 and G2 of the two unobserved regions Rn1 and Rn2 are obtained, and the line which connects the present bend coordinates and the center of gravity G1, and the line which connects the center of gravity G1 and the center of gravity G2 may be set as the bending path.

Further, in the aforementioned case of FIG. 12, the deformed bending path may be set. For example, the unobserved region Rn is divided into a plurality of regions, the representative points such as the centers of gravity are set in the plurality of divided regions, and the bending paths may be set. Further, the bending paths may be made selectable and usable by a surgeon.

According to the present invention which performs such an operation, when a dark part disappears, a suitable search method can be selected from a plurality of search methods prepared in advance in accordance with the position of the distal end portion 15 at the time point of the disappearance, more specifically, in accordance with the tube cavity site around the position.

Further, according to the present embodiment, since the bending direction of the bending portion is determined by the selected search method, and the bending portion 16 is bent and driven, search for the insertion direction can be performed more smoothly in accordance with the characteristic of the tube cavity site into which the insertion portion 11 is inserted, than the case without using the characteristic.

More specifically, when the above described tube cavity site is formed along the frontal plane, the search method which bends the bending portion 16 along the frontal plane is selected, and therefore, search for the insertion direction can be reliably performed in a short time.

Further, since when the above described tube cavity site is not formed along the frontal plane, the bending portion is bent in the bending direction in which the bending portion is not bent at that time point, and search is performed, the possibility of finding the insertion direction is high. Further, in this case, the search method can be adopted, which performs search by bending the bending portion to cover the bending direction in which the bending portion is not bent in the past, and in this case, the insertion direction can be reliably found.

Accordingly, the present embodiment also can give support so that the search for the insertion direction is performed more smoothly even when a dark part disappears in a curved body cavity.

The aforementioned configurations, procedures and the like may be modified. For example, in FIG. 3, the case of selecting the first search method is described in the case of a rectum, splenic flexure, and hepatic flexure, but the conventional search methods and the like may be made selectable and usable other than the first search method.

For example, the search method may be made also selectable, which searches for the insertion direction by bending the bending portion 16 to return to the bend coordinates of the state in which a dark part existed in the past by referring to the past bending history.

What is claimed is:

1. An endoscope apparatus comprising:
an endoscope comprising an insertion portion comprising a distal end portion and a bendable bending portion at a distal end side of the insertion portion, the insertion portion being adapted to be inserted into a body cavity of a subject;
a relative position calculation section configured to calculate a relative position with respect to the subject of the distal end portion in the body cavity of the subject;
a frontal plane direction detection section configured to detect a direction in which a frontal plane, as a plane which cuts a human body as the subject anteroposteriorly, exists;
a reference information storage section that stores in advance reference information that associates:
a plurality of characteristics including a first characteristic as to whether or not a respective plurality of tube cavity sites in an organ in a tube cavity shape in the body cavity into which the insertion portion is inserted exist along the frontal plane; and
a plurality of search methods for searching for a bending direction of the bending portion, the plurality of search methods including a first search method for searching a bending direction of the bending portion along the frontal plane, and a second search method differing from the first search method;
a selection section configured to select a search method corresponding to the relative position from the plurality of search methods, based on the relative position and on the reference information at the relative position;
a bending direction determination section configured to determine the bending direction of the bending portion according to the search method selected by the selection section; and
a bending drive section configured to bend and drive the bending portion based on the bending direction determined by the bending direction determination section.

2. The endoscope apparatus according to claim 1, wherein the plurality of characteristics include:
the first characteristic,
a second characteristic of whether or not the respective plurality of tube cavity sites are fixed in a body cavity, and
a third characteristic of whether or not the respective plurality of tube cavity sites are substantially linear.

3. The endoscope apparatus according to claim 1, wherein:
the first search method searches for the bending direction to be an insertion direction in which the distal end portion should be inserted so that the bending portion is bent and driven along the frontal plane, and
the second search method searches for the bending direction to be the insertion direction that is not in a direction in which the bending portion has been bent and driven in the past with reference to a bending history of the bending portion.

4. The endoscope apparatus according to claim 1, wherein:
when the selection section selects the first search method in which the first characteristics of tube cavity sites read out from the reference information storage section is associated to a characteristics existing along the frontal plane, the bending direction determination section determines the bending direction of the bending portion as a direction in which the frontal plane exists, and
the bending drive section bends and drives the bending portion so that the bending portion is along the frontal plane based on the bending direction determined by the bending direction determination section.

5. The endoscope apparatus according to claim 1, wherein:
the bending direction determination section determines the bending direction of the bending portion based on the direction in which the frontal plane exists, and
the bending drive section bends and drives the bending portion so that the bending portion is along the frontal plane based on the bending direction determined by the bending direction determination section.

6. The endoscope apparatus according to claim 1, further comprising:
a direction detection section which detects a direction of the frontal plane with respect to the bending portion, from the relative position,
wherein:
the bending direction determination section determines the bending direction based on the direction of the frontal plane with respect to the bending portion detected by the direction detection section, and
the bending drive section bends and drives the bending portion based on the bending direction determined by the bending direction determination section.

7. The endoscope apparatus according to claim 1, further comprising:
a direction detection section which detects a direction of the frontal plane with respect to the bending portion, from the relative position,
wherein:
the bending direction determination section determines the bending direction of the bending portion based on the direction of the frontal plane detected by the direction detection section, and
the bending drive section bends and drives the bending portion so that the bending portion is along the frontal plane based on the bending direction determined by the bending direction determination section.

8. The endoscope apparatus according to claim 1, further comprising:
a bent shape detection section which detects a bent shape of the bending portion; and
a bend coordinates storage section which stores bend coordinates information of the bent shape of the bending portion detected by the bent shape detection section,
wherein the bending drive section bends and drives the bending portion toward a direction in which the bending portion is not bent in a past based on the information stored in the bend coordinates storing section.

9. The endoscope apparatus according to claim 1,
wherein the reference information storage section includes an information storage section which stores information for identifying a tube cavity site in a tube cavity shape around the relative position from the relative position, and
wherein the selection section automatically selects a search method set in advance from the plurality of search methods in accordance with an identified tube cavity site.

10. The endoscope apparatus according to claim 1, wherein the bending direction determination section determines the bending direction of the bending portion based on the direction in which the frontal plane exists which is detected by the frontal plane direction detection section.

11. The endoscope apparatus according to claim 1, further comprising: an image pickup element provided at the distal end portion,
a dark part detection section configured to detect a dark part from an endoscopic image provided by the image pickup element,
wherein when the dark part detection section cannot detect the dark part, the selection section selects the first or second search method from the plurality of search methods with reference to the information of the relative position when the dark part cannot be detected and the reference information.

12. The endoscope apparatus according to claim 1, wherein:
the reference information storage section selects the first search method in the case of a characteristic in which the respective plurality of tube cavity sites exist along the frontal plane, and
the reference information storage section records information for selecting the second search method as the reference information in the case of a characteristic in which the respective plurality of tube cavity sites do not exist along the frontal plane.

13. The endoscope apparatus according to claim 12, wherein the selection section selects, from the relative position calculated by the relative position calculation section from the reference information storage section, the first search method or the second search method associated with the first characteristic possessed by tube cavity sites in the periphery of the relative position.

14. The endoscope apparatus according to claim 1, wherein the frontal plane direction detection section comprises a plurality of sensors configured to be mounted on a plane along the frontal plane on a body surface of the subject in which the insertion portion is inserted.

* * * * *